(12) United States Patent
Dirac et al.

(10) Patent No.: US 11,833,325 B2
(45) Date of Patent: *Dec. 5, 2023

(54) SPRINKLER CANNULA

(71) Applicant: UNOMEDICAL A/S, Birkeroed (DK)

(72) Inventors: Holger Dirac, Birkerod (DK); John Myhre Frederiksen, Borup (DK); Soren Thorup, Frederiksberg C (DK); Bo L. Justesen, Ringsted (DK)

(73) Assignee: Unomedical A/S, Lejre (DK)

( * ) Notice: Subject to any disclaimer, the term of this patent is extended or adjusted under 35 U.S.C. 154(b) by 259 days.

This patent is subject to a terminal disclaimer.

(21) Appl. No.: 17/325,375

(22) Filed: May 20, 2021

(65) Prior Publication Data

US 2021/0268181 A1 Sep. 2, 2021

Related U.S. Application Data

(63) Continuation of application No. 13/823,236, filed as application No. PCT/EP2011/067066 on Sep. 30, 2011, now Pat. No. 11,020,526.

(60) Provisional application No. 61/389,595, filed on Oct. 4, 2010.

(30) Foreign Application Priority Data

Oct. 4, 2010 (EP) .................................... 10186437

(51) Int. Cl.
| *A61M 5/158* | (2006.01) |
|---|---|
| *A61M 5/32* | (2006.01) |
| A61M 25/00 | (2006.01) |
| A61M 5/142 | (2006.01) |

(52) U.S. Cl.
CPC .......... *A61M 5/158* (2013.01); *A61M 5/3291* (2013.01); *A61M 25/007* (2013.01); *A61M 25/0015* (2013.01); *A61M 2005/14252* (2013.01); *A61M 2005/1586* (2013.01)

(58) Field of Classification Search
CPC ...... A61M 5/14; A61M 5/158; A61M 5/3291; A61M 2005/14252; A61M 25/0015; A61M 25/003; A61M 25/0068; A61M 2025/0081; A61M 2025/0253
See application file for complete search history.

(56) References Cited

U.S. PATENT DOCUMENTS

| 11,027,058 | B2 | 6/2021 | Lanier, Jr. et al. |
| 11,173,242 | B2 | 11/2021 | Lanigan et al. |
| 11,318,249 | B2 | 5/2022 | Kamen et al. |
| 11,357,910 | B2 | 6/2022 | Kamen et al. |
| 11,364,335 | B2 | 6/2022 | Lanigan et al. |
| 11,404,776 | B2 | 8/2022 | Blumberg, Jr. |
| 11,478,623 | B2 | 10/2022 | Lanigan et al. |
| 2021/0228798 | A1 | 7/2021 | Kamen et al. |

(Continued)

*Primary Examiner* — Jason E Flick
*Assistant Examiner* — Justin L Zamory
(74) *Attorney, Agent, or Firm* — Taft Stettinius & Hollister LLP; Ryan O. White; Derek B. Lavender

(57) ABSTRACT

An infusion device (50) incl. a preferably soft cannula (1) configured to be inserted by means of an insertion needle. The cannula has a tubular body member having a proximal end and a subcutaneously placed distal portion having a distal end where the distal portion is provided with an opening (2) allowing a portion of a drug conveyed through the tubular body member to discharge. The cannula further comprise, in the distal portion, a radial opening allowing a portion of a drug conveyed through the tubular body member to discharge.

20 Claims, 6 Drawing Sheets

(56) References Cited

U.S. PATENT DOCUMENTS

| | | |
|---|---|---|
| 2021/0236721 A1 | 8/2021 | Skutnik et al. |
| 2021/0252215 A1 | 8/2021 | Kamen et al. |
| 2021/0290861 A1 | 9/2021 | Grant et al. |
| 2021/0338926 A1 | 11/2021 | Kamen et al. |
| 2021/0361858 A1 | 11/2021 | Lanier, Jr. et al. |
| 2021/0393870 A1 | 12/2021 | Kessel et al. |
| 2022/0211937 A1 | 7/2022 | Kamen et al. |
| 2022/0265918 A1 | 8/2022 | Kamen et al. |
| 2022/0362467 A1 | 11/2022 | Kamen et al. |

SPRINKLER CANNULA

CROSS-REFERENCE TO RELATED APPLICATIONS

This application is a continuation application of U.S. patent application Ser. No. 13/823,236, filed Jun. 10, 2013, having the title "Sprinkler Cannula", which claims the benefit under 35 U.S.C. § 371 of International Application No. PCT/EP2011/067066, filed Sep. 30, 2011, which claims the benefit of U.S. Provisional Application Ser. No. 61/389,595, filed Oct. 4, 2010 and European Application No. 10186437.9, filed Oct. 4, 2010, each of which are incorporated by reference herein in their entirety.

The present invention relates to an infusion device configured for introduction of a fluid drug into the human body. Specifically, the present invention relates to an infusion including a cannula configured for this purpose.

According to one aspect, the present invention relates to an infusion device including a cannula having a tubular body member with a proximal end and a subcutaneously placed distal portion having a distal end. The distal portion is provided with a radial opening allowing a portion of a drug conveyed through the tubular body member to discharge.

In general terms, an infusion device inter alia comprises following sub components: a hub like part comprising a body of hard material fastened to a patients skin via a mounting pad, a pump, and a cannula.

The proximal portion of a cannula is in this specification defined as a portion placed above the skin surface of the patient during use, and the distal portion of a cannula is in this specification defined as the portion which, after mounting, is placed subcutaneously i.e. below the skin surface of the patient. The distal end opening will normally be open allowing fluid to discharge, however according to certain applications and embodiments, the opening may be closed thereby increasing the fluid pressure on the radial opening or openings.

BACKGROUND

Hypodermic cannulas or needles have been used to introduce fluid drugs to the body of human beings as well as animals for over a century.

The use of these cannulas for this purpose has long been the method of last resort, especially for the injection of medications because of the pain associated with the forcing of the needle into the body. Over the years, manufacturers of these cannulas learned that the smaller the diameter of the cannula, and the sharper the point of the introducing needle, the more comfortable the injection would be, and as a consequence, it is today common practise to inject drugs by means of very fine cannulas.

There is, however, a limit to the degree to which the diameter of these cannulas may be reduced. One limitation is established by the flow rate of fluid drug along the cannula which is related to the fourth power of the diameter of the conduit. As the diameter is reduced, the flow rate, at similar pressure, rapidly decreases. If a certain volume of fluid is to be injected and the diameter of the conduit to be reduced, either the pressure used to move the fluid along within the cannula, or the time allotted for introducing the fluid, will increase. Fluids such as insulin for treatment of diabetes are usually injected in the home by the patent. Such individuals may be unable to exert sufficient pressure to inject their insulin in a satisfactorily short period of time if the diameter of the cannula is too small.

One way to increase the flow rate of a fluid passing through a cannula is to place openings along the side of the needle. Such needles, known as sprinkler needles, are known in the art and are described, for example, by Gross in U.S. Pat. No. 6,261,272. The additional openings on the side of the needle provide additional access to the tissue creating a shorter fluid path to the tissue and also increasing the area of access to the tissue whereby the effective area of the outlet of the needle is increased. These advantages exist both in the delivery of the fluid to the tissue and in the extraction of fluid from the tissue.

A direct result of the sprinkler needle being able to deliver the fluid to a larger volume or area of tissue is a reduction of the pressure required to deliver the fluid. Further, and equally important, increasing the surface area of tissue exposed to the fluid enhances the absorption rate of the fluid by the body.

GB 2459101 A discloses a subcutaneous port and fenestrated catheter for the administration of fluids subcutaneously to be infused over a large volume of tissue. The port contains a subcutaneous chamber covered by a septum through which fluid is received from a hypodermic needle. The chamber has an exit hole with a nipple which connects to a catheter which has perforations. The port and catheter is implanted under the skin of the patient. According to the document, the port may have more than one exit hole connected to other catheters. GB 2459101 A is considered to represent relevant prior art with respect to the present invention because the reference is directed to frequent subcutanous infusion of a medicament by means of a cannula or catheter comprising one or more radial openings such that the fluid administered are received by a large tissue area.

US 2007/0129691 A disclose a laminated sprinkler needle for introduction and extraction of liquids from an animal. The needle comprising a substrate, a micro machined photo resistive layer and a micro porous layer. The structure is of simple construction and fabrication and, according to the document, provides higher flow rates than standard hollow cannulas.

While sprinkler needles have a performance advantage over straight cannula needles, this performance advantage comes at a significantly higher manufacturing cost. The additional openings must be cut in the sides of the needle which requires more time for manufacturing as well as additional manufacturing setups, and further, the openings must further be deburred in order to make sure the pain of insertion is low.

US 2005/0107743 A disclose an infusion set comprising a base member, an introducer cap and an infusion cap. The base member comprises a soft cannula extending from a lower side of the base member and a port on an upper side thereof. The port is configured to be in fluid communication with the soft cannula. The port also comprises a septum adapted to seal the port against unwanted fluid flow. The introducer cap is adapted to be mounted to the base member and has a needle adapted to extend through the septum and said soft cannula in an assembled position.

The infusion cap comprises a lumen adapted to receive a flexible tube. The infusion cap also comprises a hard cannula adapted to be inserted through the septum and to place said soft cannula in fluid communication with said lumen. The soft cannula according to US 2005/0107743 A give rise to two problems, one being that the soft cannula is disposed for kinking and the another is that the soft cannula according to US 2005/0107743 A suffers from similar delivery restrictions as already mentioned above.

WO 2002/083228 A2 discloses a fairly advanced syringe or catheter system capable of injecting, manually or automatically; precisely measured quantities of liquids into a body. A plurality of needle designs is disclosed and according to the reference, the designs create advantageously shaped or diffused clouds, streams, or jets of medicament and the like. Generally, the reference seeks to set forth a syringe or catheter allowing for controlled injection of a medicament without substantial damage to tissue. According to the reference, the teachings of the reference may be applied to a relatively long and soft catheter or a rigid needle.

WO 2004/024219 A1 discloses a method and apparatus for epidermal or intradermal delivery of a medicament. A needle having at least one side port is used to penetrate the skin of a subject. The medicament is delivered through the side port and into the skin.

US 2010/0022956 A, by the applicant of the present invention, discloses an infusion set improvable by the teachings of the present application.

An infusion device comprising a cannula to be inserted by means of an insertion needle having following characteristics is much desired:

The cannula which is cheap and simple to manufacture,
The cannula which is user friendly and cause as little pain as possible to the end user, and
The cannula which is configured such that it will mitigate the effects of kinking.

BRIEF DESCRIPTION OF THE INVENTION

The present invention seeks generally to improve today's infusion devices such that the abovementioned insufficiencies and drawbacks of today's infusion devices are overcome.

Up to this day, prior art has failed to teach a simple and yet reliable and inexpensive infusion device which in a safe and reliable manner, without substantially increasing the cost of the device, is able to satisfy the abovementioned much desired characteristics of the mentioned infusion device.

According to the invention, there is provided an infusion device as per the introductory part of this specification, and in particular, upon configuring the infusion device such that the infusion device further comprise a hub part configured to be fastened onto an outside surface of a patients skin via a mounting pad, an infusion device resolving the abovementioned drawbacks are provided.

According to one embodiment, the infusion device may further include a pump configured to be in fluid connection with a reservoir configured to store or hold medication.

According to one embodiment, the subcutaneously placed distal portion may be made from soft material.

According to one embodiment, the cannula may be configured to be inserted by means of an insertion needle.

According to one embodiment the radial opening or openings may, when the cannula is inserted, be provided at least 1 millimeter below the skin surface.

According to one embodiment, the radial opening or openings may, when the cannula is inserted, be provided no more than 9 millimeter below the skin surface.

According to one embodiment, the radial opening may, when the cannula is inserted, be provided below the basal membrane.

According to one embodiment, the radial opening or openings may, when the cannula is inserted, be provided no more than 3 millimeter below the skin surface.

According to one embodiment, the cannula may further comprise a plurality of radial openings allowing a portion of a drug conveyed through the tubular body member to discharge.

According to one embodiment, the radial openings may be apportioned such that the radial openings extend only through one wall of the tubular body member. Further, the radial openings may or may not extend axially along a straight line along the tubular body member.

According to one embodiment, one or more radial openings may extend through the tubular body member in an angle lying approximately perpendicular to a longitudinal axis of the cannula.

According to one embodiment, one or more radial openings may extend through the tubular body member in at least one angle oriented different from an angle lying perpendicular to a longitudinal axis of the cannula.

According to one embodiment, the radial openings that may extend through the tubular body member may have substantially equal diameter.

According to one embodiment, the radial openings that may extend through the tubular body member may have varying diameter.

According to one embodiment, the radial openings which may have varying diameter may be arranged such that the opening having the largest diameter is arranged nearest the distal portion of the cannula.

According to one embodiment, the radial openings, which may have varying diameter, further may be arranged such that the radial opening having the smallest diameter is arranged nearest the proximal end of the cannula.

According to one embodiment, the length of the distal portion of the cannula may be less than 15 mm and the outer diameter of the distal portion may be less than 1.5 mm and the diameter of the one or more radial openings may be between 15 μm and 0.3 mm.

According to one embodiment, the infusion device may be configured for subcutaneous infusion of drugs such as insulin and the like.

In another embodiment, there is provided an infusion cannula to convey subcutaneous infusion of a drug. The infusion cannula includes a tubular body defining a conduit extending along a longitudinal axis of the tubular body, wherein the tubular body includes a proximal end and a subcutaneously placed distal portion having a wall and a distal end, and wherein the distal portion includes a soft material and the distal end is tapered. The distal portion further includes at least two radial openings extending through the wall of the distal portion to the conduit and an outlet at the distal end, wherein the at least two radial openings of the tubular body allow a portion of the drug conveyed through the tubular body to discharge into subcutaneous tissue of an individual. Two of the at least two radial openings are not located opposite each along the longitudinal axis and are offset from each other with respect to an angle seen from the outlet. A length of the distal portion of the tubular body permits a portion of an insertion needle to extend past the outlet of the distal end during placement of the infusion cannula.

In a further embodiment, there is provided an infusion device to convey subcutaneous infusion of a drug. The infusion device includes a cannula having a tubular body defining a conduit extending along a longitudinal axis of the tubular body. The tubular body includes a proximal end and a subcutaneously placed distal portion having a wall and a distal end, wherein the distal portion comprises a soft material and the distal end is tapered. The distal portion further includes at least two radial openings extending through the wall of the distal portion and an outlet at the distal end wherein the at least two radial openings of the tubular body allow a portion of the drug conveyed through the tubular body to discharge into subcutaneous tissue of an individual. Two of the at least two radial openings are not located opposite each along the longitudinal axis and are offset from each other with respect to an angle seen from the outlet. A length of the distal portion of the tubular body permits a portion of an insertion needle to extend past the outlet of the distal end during placement of the infusion cannula. A hub part is configured to be coupled to the cannula and fastened onto an outside surface of a patient's skin via a mounting pad.

DETAILED DESCRIPTION OF THE INVENTION WITH REFERENCE TO THE FIGURES

Figure 1:
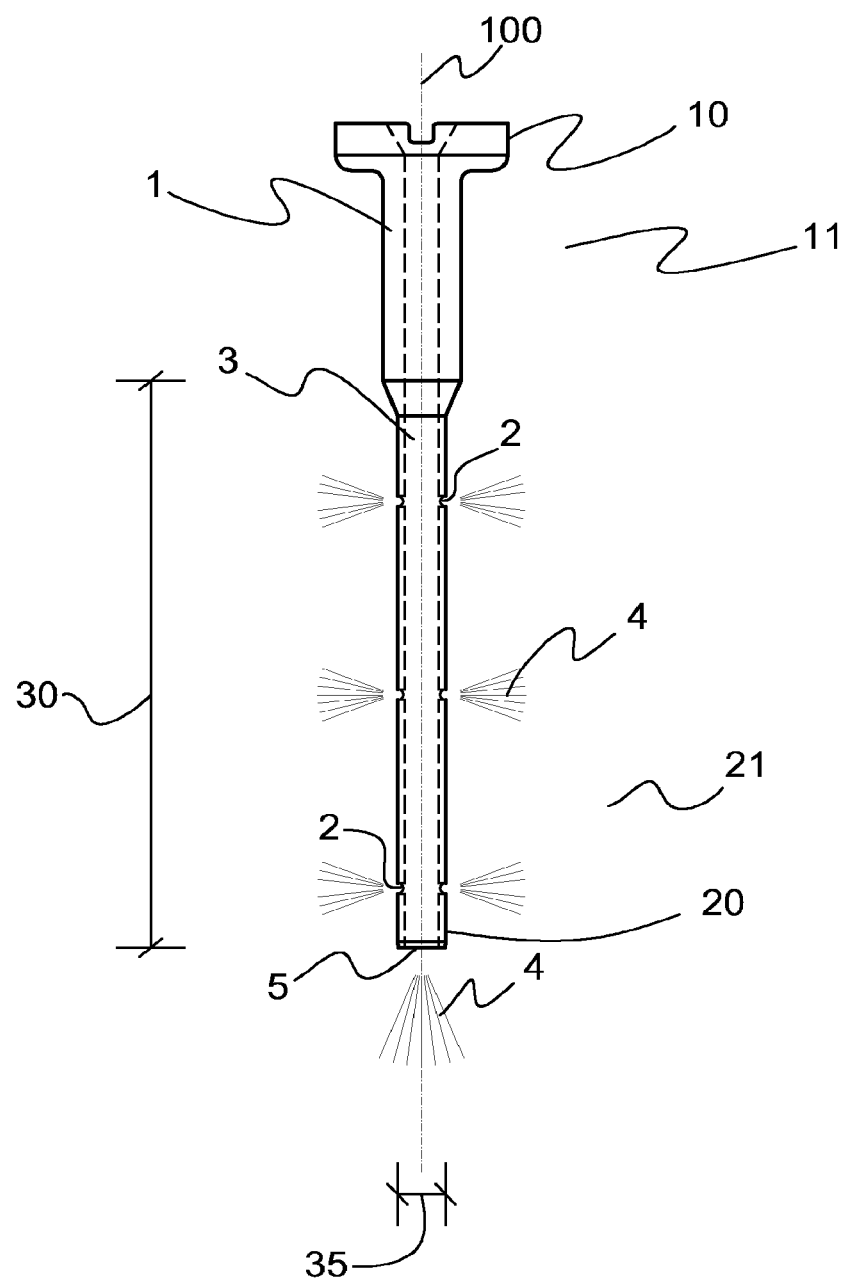
FIG. 1 is a plane view of an embodiment of a cannula applicable to the infusion device according to the present invention.

FIG. 1 shows a plane view of one embodiment of a cannula 1 applicable to an infusion device according to the present invention. The remaining parts and components of the infusion device is considered well known to those skilled in the relevant art, and therefore, such parts and components will only be briefly described in this specification, see FIG. 2.

Figure 3:
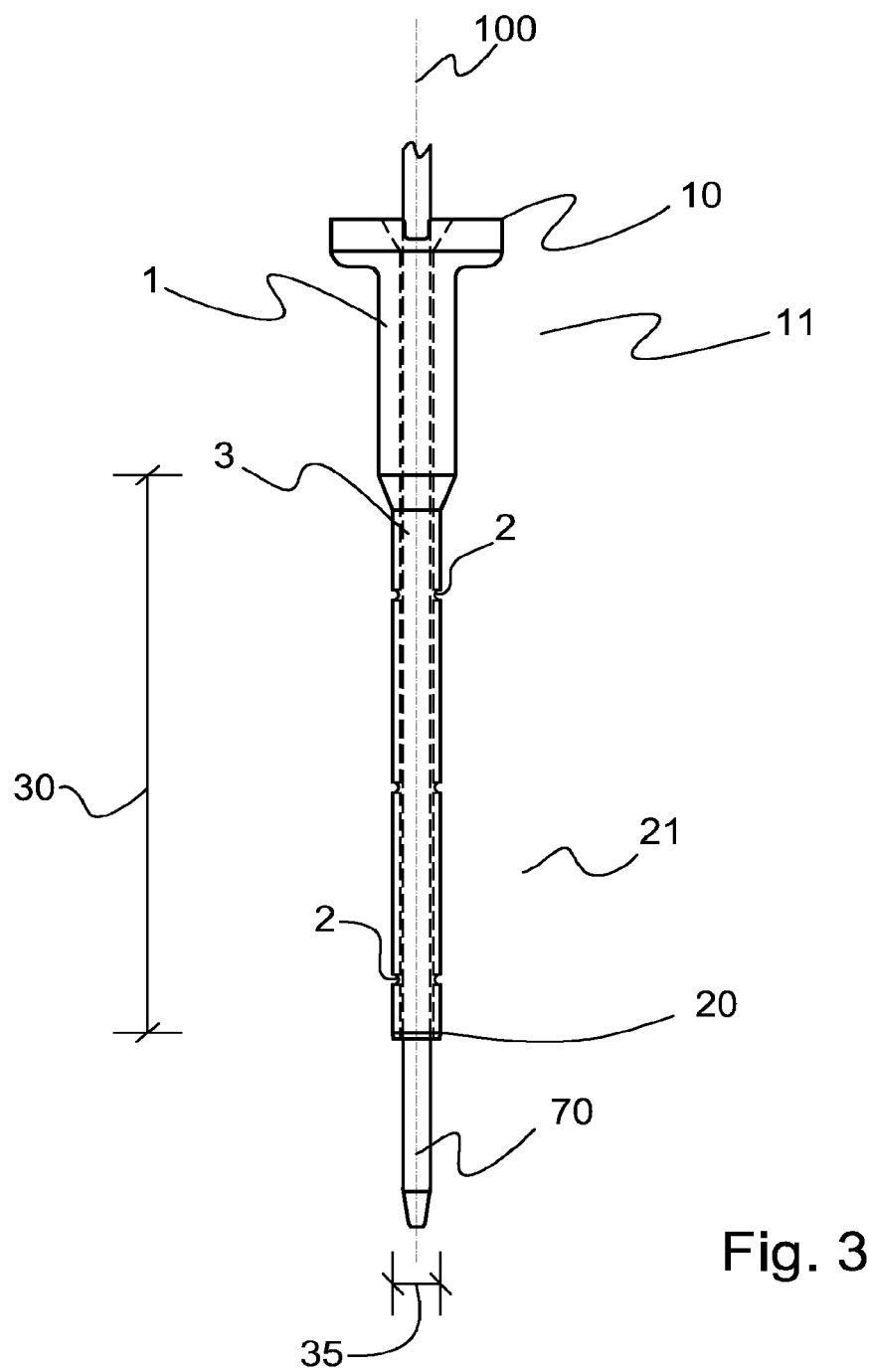
FIG. 3 is a plane view of a cannula applicable to the infusion device according to the present invention, here shown together with a part of an insertion needle.

As can be seen in FIG. 1 the cannula 1 is provided with a tubular body member 3 having a conduit shown by the dashed lines. The conduit interconnects the in this figure not shown infusion device with the openings 2 and 5. The cannula 1 includes a proximal end 10 configured for interconnection with the not shown infusion device as well as a distal portion 21 configured for subcutaneously placement by means of the insertion needle 70 shown in FIG. 3.

Numeral 5 refers to an outlet arranged in the distal portion 21, opposite the interconnection with the infusion device. The outlet 5 may or may not be considered the primary outlet for drugs 4. In addition to the outlet 5, the cannula 1 is provided with at least one further opening 2.

Figure 4:
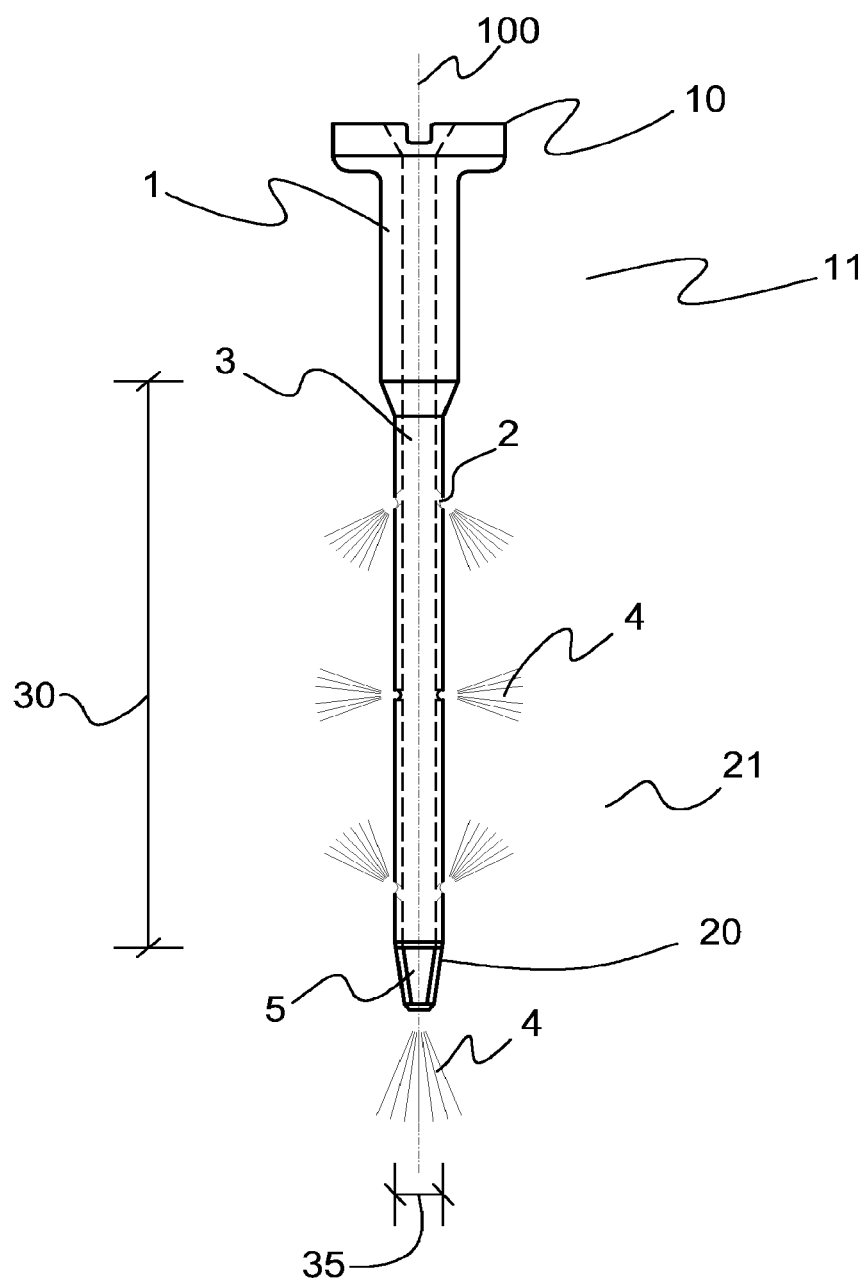
FIG. 4 is a plane view of an embodiment of a cannula applicable to the infusion device according to the present invention
Figure 5:
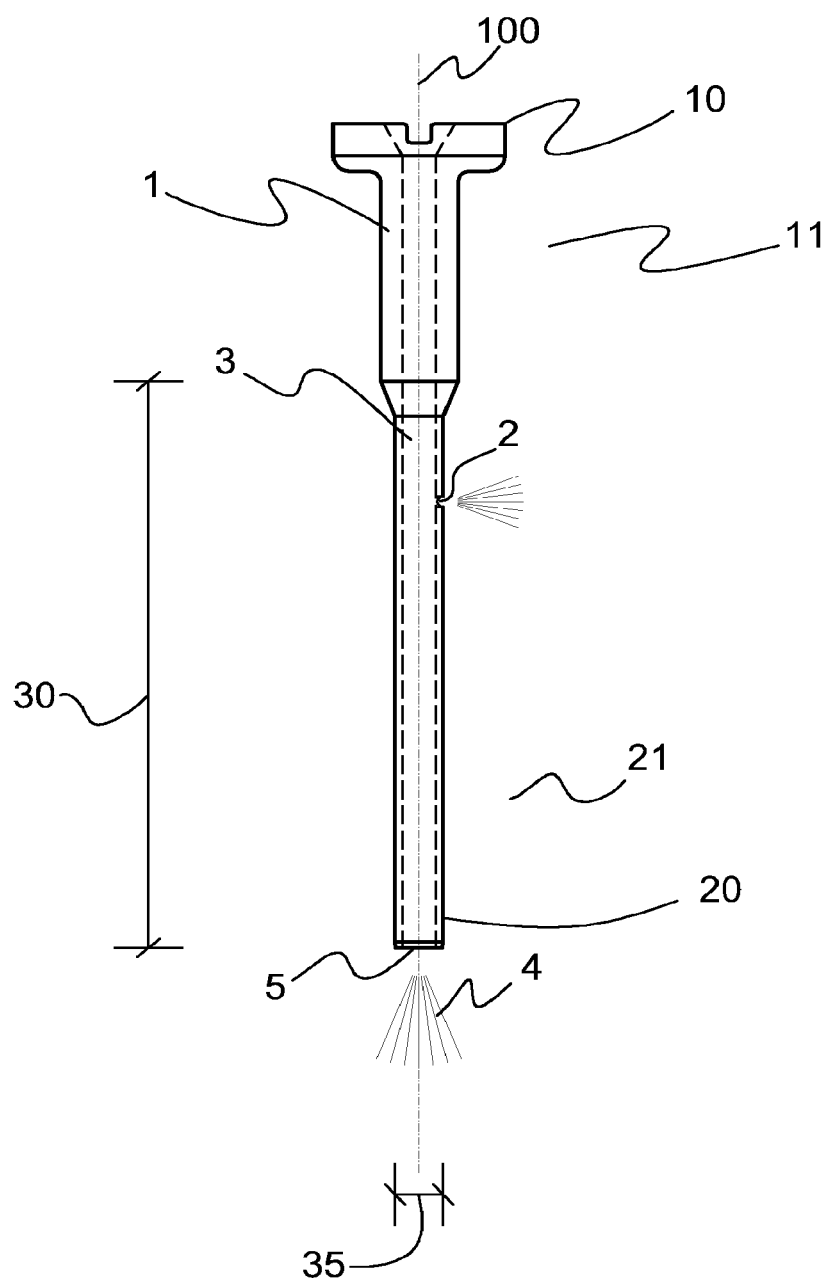
FIG. 5 is a plane view of an embodiment of a cannula applicable to the infusion device according to the present invention.

Although FIGS. 1-4 disclose the cannula 1 including a plurality of openings 2, the present invention is not in any way limited to embodiments of the cannula 1 comprising more than one opening 2, see FIG. 5.

The subcutaneously placed distal portion 21, alternatively the entire cannula 1, may be made from a soft material such as PTFE (Teflon), FEP, rubber, PE material or silicone base materials and the like.

At least one of the radial openings 2 may, when the cannula 1 is inserted, be provided at between 1 and 9 millimeter below the skin surface 55, see FIG. 2.

Figure 2:
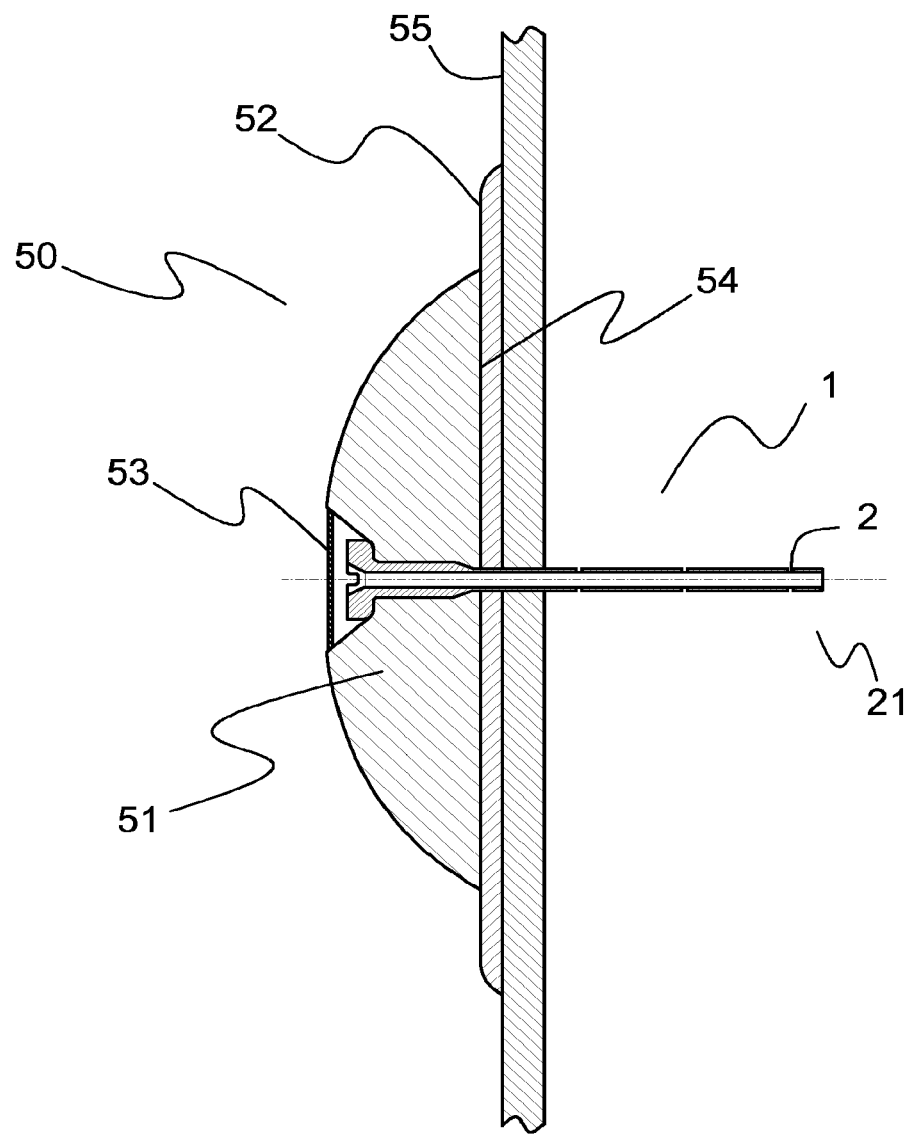
FIG. 2 is an infusion device according to the present invention.

FIG. 2 illustrates schematically an infusion device according to the present invention. The infusion device 50 includes a cannula 1 having a tubular body member 3 with a proximal end 10 and a subcutaneously placed distal portion 21 having a distal end 20. The distal portion 21 of the cannula may be provided with a radial opening 2 allowing a portion of a drug 4 conveyed through the tubular body member 3 to discharge.

The infusion device according to FIG. 2 further include a hub part 51 configured to be fastened onto an outside surface of a patients skin 55 via a mounting pad 52. The mounting pad 52 may be provided with an adhesive layer, configured to adhere to a patient's skin, and a not shown removable release liner which covers the adhesive layer. The mounting pad 52 may be a dressing, a plaster, an adhesive pad or the like and the mounting pad may be configured in various shapes such as oval, circular, triangular rectangular etc.

According to one embodiment, the infusion device may include a hub part 51 having a main plane being essentially parallel to the skin of the patient, when the infusion set is attached to a patient. The hub part 51 may have a main 54 surface being closest to the skin of a patient, and the main surface may be provided with fastening means such as the mounting pad 52 for fastening the infusion device to the skin 55 of a patient.

In the embodiment according to FIG. 2, the cannula 1 extends from the hub part 51 through the fastening means or mounting pad 52. Alternatively, the cannula 1 may extend from the hub part 51 of the infusion device essentially along an inclined axis of insertion (not shown).

As shown in FIG. 2, the hub part 51 may include a septum or barrier 53.

As can be seen in FIGS. 1-4, the cannula 1 may be provided with a plurality of radial openings 2 allowing the drug 4, conveyed through the tubular body member or hollow 3, to discharge. The openings 2 may be apportioned such that the openings 2 extend through one wall of the tubular body member 3 only, see FIG. 4. Further, the radial openings 2 may extend axially along a not shown straight line along the cannula 1. The radial openings 2 may, in other embodiments, be placed on different quarters of the cannula 1 such that all the holes are not blocked when pressure is applied to one side of the cannula 1.

The opening or openings 2 may or may not extend through said tubular body member in an angle lying approximately perpendicular to a longitudinal axis of the cannula 1. Further, the opening or openings 2 may extend through the tubular body member in at least one angle oriented different from an angle lying perpendicular to the longitudinal axis 100 of the cannula 1, as shown in FIG. 4.

The angles may constitute any angle between 0° and 180° relative to the longitudinal axis 100; however, angles lying in-between 30° and 150°, alternatively 60° and 120° or even 90° may be preferred.

The radial opening or openings 2 may have substantially equal diameter, although this is not in any way a requirement of the present invention. The opening or openings 2 may, according to certain embodiments, also have varying diameter.

It may be preferred to apply the radial opening or openings 2 as a spherical opening or openings; however other forms of opening or openings may equally be applied as long as the opening or openings do not adversely affect the strength and functionality of the cannula 1.

In case the cannula is provided with radial openings 2 having varying diameter, the openings 2 may be arranged such that the opening 2 having the largest diameter is arranged nearest the distal portion 21 of the cannula 1, whereby a substantially uniform outlet of fluid may be obtained over the length of the cannulas distal portion 21.

The length 30 of the distal portion 21 of the cannula 1 may be less than 30 mm, preferably 15 mm, and the outer diameter 35 of the distal portion 20 may be less than 2 mm, preferably less than 1.5 mm and the diameter of the opening or openings 2 may be between 10 μm and 0.5 mm, preferably between 25 μm and 0.3 mm.

The distal end 20 of the cannula 1 may or may not be tapered such as shown in FIG. 4. Providing the distal end 20 of the cannula 1 with a tapered end may facilitate insertion of the cannula 1. Although only the embodiment according to FIG. 4 is shown with a slant and tapered end, this may not in any way be considered limiting to other embodiments according to this specification.

Figure 6:
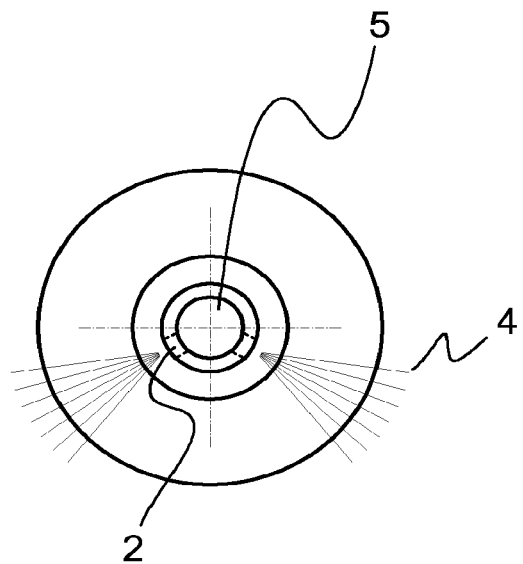
FIG. 6 is an end view of an embodiment of a cannula applicable to the infusion device according to the present invention.

The number of radial openings may, as already mentioned, vary from only one, such as shown in FIG. 5, to any number of openings, however according to one preferred embodiment, the cannula is provided with two radial openings, such as shown in the end view according to FIG. 6.

According to a well functioning embodiment, the cannula may be provided with two radial openings, or sprinkler holes, which are not located opposite each other, i.e. the openings are offset longitudinally as well as with respect to an angle seen from the end or circular cross section. A well functioning angle between the opening are considered to be 120 degree, see FIG. 6.

The opening or openings may be provided, by means of drilling, punching, cutting or equivalent, in any angle to the longitudinal axis 100 of the cannula 1.

Generally seen, the cannula for the infusion device according to the present invention allows a drug such as insulin to be absorbed faster in the blood of the patient than the "one-outlet" soft cannulas according to today's infusion devices comprising cannulas made from a soft material.

According to certain aspects of the present invention, it has been found that one or more radial openings reduce soft cannulas well known tendency to occlude, e.g. due to kinking. Hence the cannula for the infusion device according to the present invention is less inclined to malfunction as a result of kinking.

The application and combination of features and solutions presented by the present invention is not limited to the presented embodiments. One or more features of one embodiment can and may be combined with one or more not disclosed features of other embodiments, whereby not described, but valid, embodiments of the present invention may be obtained. One example is that the cannula according to the present invention may form part of an infusion device provided with means for monitoring or asserting whether or not the cannula of the infusion set is inserted as intended. Such means could inter alia constitute means configured for measuring impedance, where one option of performing the measurement by means of measuring impedance could be by using a drug such as insulin present in the cannula as an electrode.

The term "comprises/comprising/comprised of" when used in this specification incl. claims is taken to specify the presence of stated features, integers, steps or components but does not preclude the presence or addition of one or more other features, integers, steps, components or groups thereof.

The invention claimed is:

1. An infusion cannula to convey subcutaneous infusion of a drug, the infusion cannula comprising:
   a tubular body defining a conduit extending along a longitudinal axis of the tubular body, the tubular body including a proximal end and a subcutaneously placed distal portion having a wall and a distal end, wherein the distal portion comprises a soft material and the distal end is tapered;
   wherein the distal portion further includes at least two radial openings extending through the wall of the distal portion to the conduit and an outlet at the distal end, the at least two radial openings of the tubular body allowing a portion of the drug conveyed through the tubular body to discharge into subcutaneous tissue of an individual;
   wherein two of the at least two radial openings are not located opposite each other along the longitudinal axis and are offset from each other with respect to an angle seen from the outlet; and
   wherein a length of the distal portion of the tubular body permits a portion of an insertion needle to extend past the outlet of the distal end during placement of the infusion cannula.

2. The infusion cannula of claim 1 wherein the soft material comprises a material selected from one of PTFE, FEP, rubber, PE material or silicone base materials and wherein the at least two radial openings reduce occlusion due to kinking of the tubular body.

3. The infusion cannula of claim 2 wherein a length of the distal portion of the tubular body is less than 15 mm to permit the portion of the insertion needle to extend past the outlet of the distal end during placement of the infusion device.

4. The infusion cannula of claim 3 wherein the angle between the two of the at least two radial openings is substantially 120 degrees.

5. The infusion cannula of claim 4 wherein the diameter of the two of the at least two radial openings is between 10 μm and 0.5 mm.

6. The infusion cannula of claim 4 wherein the diameter of the two of the at least two radial openings is between 25 μm and 0.3 mm.

7. The infusion cannula of claim 4 wherein the outlet at the distal end has an outer diameter of less than 1.5 mm.

8. The infusion cannula of claim 1 wherein the two of the at least two radial openings extending through the wall have substantially equal diameter.

9. The infusion cannula of claim 1, wherein the two of the at least two radial openings extending through the wall have varying diameters.

10. The infusion cannula of claim 1, wherein the two of the at least two radial openings extending through the wall are configured such that the radial opening having a smallest diameter is arranged nearest the distal portion of the tubular body.

11. The infusion cannula of claim 1, wherein the two of the at least two radial openings extending through the wall are configured such that the radial opening having a smallest diameter is arranged nearest the proximal end of the tubular body.

12. An infusion device to convey subcutaneous infusion of a drug, the infusion device comprising:
   a cannula including a tubular body defining a conduit extending along a longitudinal axis of the tubular body, the tubular body including a proximal end and a subcutaneously placed distal portion having a wall and a distal end, wherein the distal portion comprises a soft material and the distal end is tapered;

wherein the distal portion further includes at least two radial openings extending through the wall of the distal portion and an outlet at the distal end, the at least two radial openings of the tubular body allowing a portion of the drug conveyed through the tubular body to discharge into subcutaneous tissue of an individual;

wherein two of the at least two radial openings are not located opposite each other along the longitudinal axis and are offset from each other with respect to an angle seen from the outlet;

wherein a length of the distal portion of the tubular body permits a portion of an insertion needle to extend past the outlet of the distal end during placement of the infusion cannula; and a hub part configured to be coupled to the cannula and fastened onto an outside surface of a patient's skin via a mounting pad.

13. The infusion device of claim 12 wherein the soft material comprises a material selected from one of PTFE, FEP, rubber, PE material or silicone base materials and wherein the at least two radial openings reduce occlusion due to kinking of the tubular body.

14. The infusion device of claim 13 wherein a length of the distal portion of the tubular body is less than 15 mm to permit the portion of the insertion needle to extend past the outlet of the distal end during placement of the infusion device.

15. The infusion device of claim 14 wherein the angle between the two of the at least two radial openings is substantially 120 degrees.

16. The infusion device of claim 15 wherein the diameter of the two of the at least two radial openings is between 10 μm and 0.5 mm.

17. The infusion device of claim 15 wherein the diameter of the two of the at least two radial openings is between 25 μm and 0.3 mm.

18. The infusion device of claim 15 wherein the outlet at the distal end has an outer diameter of less than 1.5 mm.

19. The infusion device of 12 wherein the two of the at least two radial openings extending through the wall have one of: i) substantially equal diameter or ii) varying diameters.

20. The infusion device of claim 12 wherein the two of the at least two radial openings extending through the wall are configured such that the radial opening having a smallest diameter is arranged nearest the distal portion of the tubular body or the radial opening having a smallest diameter is arranged nearest the proximal end of the tubular body.

* * * * *